(12) United States Patent
Butler

(10) Patent No.: US 10,123,761 B2
(45) Date of Patent: Nov. 13, 2018

(54) DEVICE AND METHOD FOR SPATIOTEMPORAL RECONSTRUCTION OF A MOVING VASCULAR PULSE WAVE IN THE BRAIN AND OTHER ORGANS

(71) Applicant: William E. Butler, Boston, MA (US)

(72) Inventor: William E. Butler, Boston, MA (US)

( * ) Notice: Subject to any disclaimer, the term of this patent is extended or adjusted under 35 U.S.C. 154(b) by 125 days.

(21) Appl. No.: 15/200,083

(22) Filed: Jul. 1, 2016

(65) Prior Publication Data

US 2017/0000441 A1    Jan. 5, 2017

Related U.S. Application Data

(60) Provisional application No. 62/187,631, filed on Jul. 1, 2015.

(51) Int. Cl.
| | |
|---|---|
| *G06K 9/00* | (2006.01) |
| *A61B 6/00* | (2006.01) |
| *G06T 7/00* | (2017.01) |

(52) U.S. Cl.
CPC ............ *A61B 6/5217* (2013.01); *A61B 6/481* (2013.01); *A61B 6/504* (2013.01); *G06T 7/0016* (2013.01); *G06T 2207/10116* (2013.01); *G06T 2207/20064* (2013.01); *G06T 2207/30016* (2013.01); *G06T 2207/30104* (2013.01)

(58) Field of Classification Search
None
See application file for complete search history.

(56) References Cited

U.S. PATENT DOCUMENTS

2016/0220112 A1*    8/2016    Schmoll ................ A61B 3/102

\* cited by examiner

*Primary Examiner* — Atiba O Fitzpatrick
(74) *Attorney, Agent, or Firm* — Ziolkowski Patent Solutions Group, SC

(57) ABSTRACT

The brain appears to have organized cardiac frequency angiographic phenomena with such coherence as to qualify as vascular pulse waves. Separate arterial and venous vascular pulse waves may be resolved. This disclosure states the method of extracting a spatiotemporal reconstruction of the cardiac frequency phenomena present in an angiogram obtained at faster than cardiac frequency. A wavelet transform is applied to each of the pixel-wise time signals of the angiogram. If there is motion alias then instead a high frequency resolution wavelet transform of the overall angiographic time intensity curve is cross-correlated to high temporal resolution wavelet transforms of the pixel-wise time signals. The result is filtered for cardiac wavelet scale then pixel-wise inverse wavelet transformed. This gives a complex-valued spatiotemporal grid of cardiac frequency angiographic phenomena. It may be rendered with a brightness-hue color model or subjected to further analysis.

6 Claims, 5 Drawing Sheets

DEVICE AND METHOD FOR SPATIOTEMPORAL RECONSTRUCTION OF A MOVING VASCULAR PULSE WAVE IN THE BRAIN AND OTHER ORGANS

CROSS-REFERENCE TO RELATED APPLICATIONS

This application claims the benefit from U.S. Provisional Application No. 62/187,631 filed Jul. 1, 2015, which is hereby incorporated by reference in its entirety for all purposes as if fully set forth herein.

FIELD OF THE DISCLOSURE

The disclosure is directed to a method for spatiotemporal reconstruction of a moving vascular pulse wave in the brain and other organs. The disclosure is further directed to a device for spatiotemporal reconstruction of a moving vascular pulse wave in the brain and other organs. This disclosure is motivated by the desire to reconstruct the motions of vascular pulse waves in the brain. The same methods can apply to any organ with a blood supply.

BACKGROUND OF THE DISCLOSURE

The heart sends blood to the brain as a sequence of stroke volumes. Yet the equivalent volume of blood that moves to the brain with each heart beat has a measurable mortality if freely released into the cranial cavity. This implies that the brain has a set of adaptations that enables it to handle the volume and kinetic energy load attached to each heartbeat of blood that enters the brain. The ventricles of the brain, which hold spinal fluid, remain the largest anatomic structure in the human body without known primary purpose. A hypothesis is that they are part of the adaptations that allow the brain to handle the volume and kinetic energy of each heartbeat. To test this hypothesis one needs a method to trace spatiotemporally the cardiac frequency phenomena of each single heartbeat of a sequence of heart beats.

Accordingly, this disclosure addresses the desire to reconstruct the cardiac frequency angiographic phenomena.

SUMMARY OF THE DISCLOSURE

The foregoing needs are met, to a great extent, by the disclosure, wherein in one aspect a technique and apparatus are provided for spatiotemporal reconstruction of a moving vascular pulse wave in the brain.

In accordance with one aspect, a method of extracting cardiac frequency phenomena from an angiographic study obtained at faster than cardiac frequency. When there is an instance of no significant motion alias, the method may include a wavelet transform of a pixel-wise time signals, filtering for cardiac wavelet scale, and inverse wavelet transformation. When there is an instance of significant motion alias, the method may include a high temporal resolution wavelet transform of a pixel-wise time signals, a high frequency wavelet transform of the overall angiographic intensity curve, a pixel-wise wavelet cross correlation of these, filtering for cardiac wavelet scale, and inverse wavelet transformation. When there is an instance of no significant motion alias, the method may include receiving angiographic data consisting of n by m pixels by q frames into computer memory; reformatting the angiographic data with a processor to generate an n by m array of time signals, each q samples long; applying a complex valued wavelet transform by the processor to each pixel-wise time signal to generate an n by m array of wavelet transforms; filtering the pixel-wise wavelet transforms for cardiac frequency by the processor; performing on the pixel-wise wavelet transforms data an inverse wavelet transform by the processor into time domain and reformatting into q frames of n by m pixels; and rendering each frame as an image with a brightness hue color model to represent a complex datum in each pixel with the processor. When there is an instance of significant motion alias, the method may include summing an angiographic signal for each time frame by a processor for all n by m pixels to generate an overall angiographic intensity point for each of q frames to generate an overall angiographic time intensity curve of length q; applying a high frequency resolution wavelet transform by the processor to the angiographic time intensity curve; reformatting then angiographic data by the processor as an n by m array of time signals each of length q; performing a high temporal wavelet transformation by the processor on each pixel-wise time signal to generate an n by m array of high temporal resolution wavelet transforms; cross correlating in wavelet domain, each pixel-wise high temporal resolution wavelet transform by a single high frequency resolution wavelet transform of an overall angiographic time intensity curve by the processor; inverse wavelet transforming an n by m array of cross-correlated signals in wavelet domain to generate an n by m array of time domain time signals each of length q by the processor; and reformatting the n by m time signals of length a by the processor into q frames of n by m pixels, each complex valued.

In accordance with one aspect, a device for extracting cardiac frequency phenomena from an angiographic study obtained at faster than cardiac frequency. The device in an instance of no significant motion alias may include a processor configured to receive angiographic data consisting of n by m pixels by q frames into a computer memory; the processor further configured to reformat the angiographic data to generate an n by m array of time signals, each q samples long; the processor further configured to apply a complex valued wavelet transform to each pixel-wise time signal to generate an n by m array of wavelet transforms; the processor further configured to filter the pixel-wise wavelet transforms for cardiac frequency; the processor further configured to perform on the pixel-wise wavelet transforms data an inverse wavelet transform into time domain and reformatting into q frames of n by m pixels; and the processor further configured to render each frame as an image with a brightness hue color model to represent a complex datum in each pixel. The device may include in an instance of significant motion alias, a processor configured to sum the angiographic signal for each time frame by the processor for all n by m pixels to generate an overall angiographic intensity point for each of the q frames to generate an overall angiographic time intensity curve of length q; the processor further configured to apply a high frequency resolution wavelet transform to the angiographic time intensity curve; the processor further configured to reformat then the angiographic data as an n by m array of time signals each of length q; the processor further configured to perform a high temporal wavelet transformation on each such pixel-wise time signal to generate an n by m array of high temporal resolution wavelet transforms; the processor further configured to cross correlate in wavelet domain, each pixel-wise high temporal resolution wavelet transform by the single high frequency resolution wavelet transform of an overall angiographic time intensity curve; the processor further configured to inverse wavelet transform the n by m array of cross-correlated signals in wavelet domain to generate an n by m array of time domain time signals each of length q; and the processor further configured to reformat the n by m time signals of length a into q frames of n by m pixels, each complex valued.

There has thus been outlined, rather broadly, certain aspects of the disclosure in order that the detailed description thereof herein may be better understood, and in order that the present contribution to the art may be better appreciated. There are, of course, additional aspects of the disclosure that will be described below and which will form the subject matter of the claims appended hereto.

According to the sampling theorem of Shannon, Nyqvist and Kotelnikov, to reconstruct a phenomenon such as a vascular pulse wave that transpires are cardiac frequency, one must sample at much higher than cardiac frequency. The method of this disclosure therefore requires raw data in the form of a brain angiogram acquired at much higher than cardiac frequency. The angiographic data sources where the method of this disclosure has been demonstrated and reduced to practice include ultrasound angiography, optical angiography, and a fluoroscopic angiography.

With ultrasound angiography, an ultrasound contrast agent, such as perflutren, is injected intravenously as a bolus, and ultrasound images are obtained of the brain at much higher than cardiac rate as the perflutren bolus travels through the brain. In one aspect, while ultrasound can image at a faster rate than cardiac rate, the blockage of sound by the skull bone impedes its sensitivity for this purpose. In a piglet cranial window model, ultrasound imaging is performed through a cranial window of a passing bolus of perflutren, an ultrasound contrast agent, in the dose of 1.2 million microspheres. The ultrasound video footage recorded at 30 Hz provides a cross-sectional angiogram of the brain. Other frequencies are contemplated as well.

With optical brain surface angiography, the brain surface is exposed, an intravenous dose of indocyanine green is injected, and images of the brain surface via an infrared pass optical filter are acquired at faster than cardiac frequency. In one aspect, the brain surface optical angiography is performed as a component of craniotomy for clipping of a brain artery aneurysm. After a clip has been applied to the neck of the aneurysm to exclude blood from entering it, a brain surface optical angiogram is obtained to confirm that blood does not enter the aneurysm and that the parent vessel of origin to the aneurysm has not been compromised by application of the clip. An operating microscope may be equipped with a beam splitter. One optical channel gives both wavelength views of the operative field. The other optical channel has a near infrared pass filter. At the moment of the optical angiogram, the anesthesiologist injects 25 mg of indocyanine green (ICG), a near infrared fluorescent agent. The field is stimulated with near infrared light and the fluorescence is captured as video footage at 30 Hz. Other frequencies are contemplated as well. This optical angiogram is obtained at significantly faster than cardiac rate.

With fluoroscopic angiography, an intravascular bolus of a water soluble iodinated contrast agent is injected as fluoroscopic x-ray images are obtained at much higher than cardiac frequency. In one aspect, humans with a suspected brain aneurysm, arteriovenous malformations, or cerebrovascular occlusive disease may undergo catheter cerebral angiography to confirm a diagnosis or as a part of the delivery of therapy. The fluoroscopic unit currently in clinical use for neuroangiography at Massachusetts General Hospital, the Siemens Artiz-Zee, records x-ray fluoroscopy images at up to 30 Hz, which is faster than cardiac rate. Other frequencies are contemplated as well. A dose of iodinated contrast is injected intravascularly and the angiographic footage is obtained during its passage across the vascular bed from the arterial to the venous component.

Given an angiogram obtained at faster than cardiac rate, the next step of this disclosure is to apply a wavelet filter to yield a time varying extraction of the cardiac frequency angiographic phenomena. There is prior art for the use of wavelets in the analysis of one-dimensional signals (U.S. Pat. No. 7,035,679B2) but not as images, and as noise correction tools in biomedical imaging (U.S. Pat. No. 7,602,183B2). But there is no prior art of wavelets for spatiotemporal reconstruction of cardiac frequency phenomena in images.

However, there may be cardiac-induced pulse motion of the organ including the vasculature undergoing the angiographic study, since the kinetic energy of the heart transmitted through blood vessels and blood may produce cardiac frequency to and fro movements of vessels containing angiographic contrast. The artifact with cardiac frequency wavelet filtering produced in this fashion is termed motion alias. This disclosure includes a method for attenuating motion alias by the use of high temporal wavelet resolution wavelet transforms. This method of attenuating motion alias is distinct from those methods that employ gating to compensate for example for respiratory motion (US patent publication number 2008/0226149A1).

The use of high temporal resolution wavelet transforms however may produce another artifact, frequency alias, where non cardiac frequency phenomena pass through the high temporal resolution wavelet transform. This disclosure includes a method for the simultaneous attenuation of motion alias and frequency alias by the use of cross correlated high temporal and high frequency resolution wavelet transforms, each of different specific properties to be covered below.

In this respect, before explaining at least one aspect of the disclosure in detail, it is to be understood that the disclosure is not limited in its application to the details of construction and to the arrangements of the components set forth in the following description or illustrated in the drawings. The disclosure is capable of aspects in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the disclosure. It is important, therefore, that the claims be regarded as including such equivalent constructions insofar as they do not depart from the spirit and scope of the disclosure.

DETAILED DESCRIPTION

Figure 1:
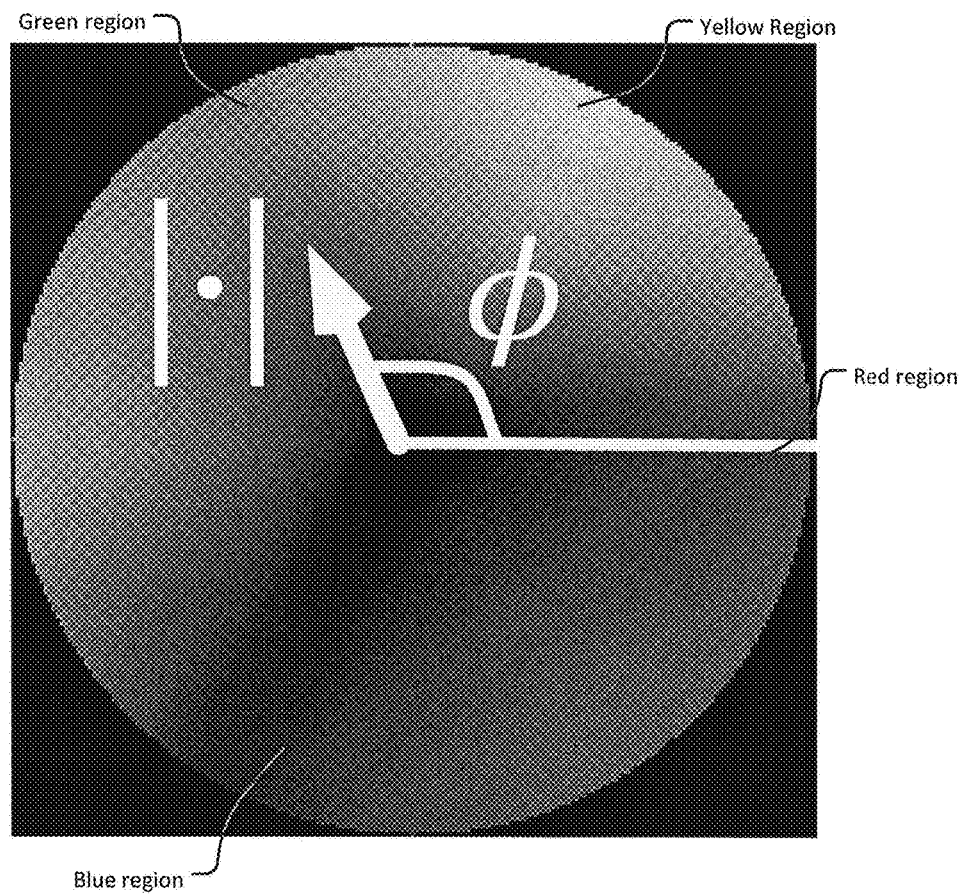
FIG. 1 illustrates a brightness hue color model for rendering a complex valued number according to aspects of the disclosure.

The disclosure will now be described with reference to the drawing figures, in which like reference numerals refer to like parts throughout. Aspects of the disclosure advantageously provide a method and device for spatiotemporal reconstruction of a moving vascular pulse wave in the brain.

The brain appears to have organized cardiac frequency angiographic phenomena with such coherence as to qualify as vascular pulse waves. Separate arterial and venous vascular pulse waves may be resolved. This disclosure states the method of extracting a spatiotemporal reconstruction of the cardiac frequency phenomena present in an angiogram obtained at faster than cardiac frequency. A wavelet transform is applied to each of the pixel-wise time signals of the angiogram. The cardiac frequency phenomena are extracted by setting to zero all wavelet coefficients except for those corresponding to cardiac wavelet scale. The result is inverse wavelet transformed pixel-wise to give a spatiotemporal grid of complex valued data representing cardiac frequency angiographic phenomena. If there is motion alias, which may be manifested by phase bimodality within the lumen of a vessel, then a modified method is applied. A high frequency resolution wavelet transform is applied to the overall angiographic time intensity curve. The pixel-wise time signals undergo each a high temporal resolution. Each of these pixel-wise high temporal resolution wavelet transforms is cross-correlated to the single high frequency resolution wavelet transform of the overall angiographic time intensity curve. The result is filtered for cardiac wavelet scale then pixel-wise inverse wavelet transformed. This gives a complex-valued spatiotemporal grid of cardiac frequency angiographic phenomena. It may be rendered with a brightness-hue color model or subjected to further analysis.

This disclosure is distinct from the common method of reconstructing cardiac frequency phenomenon by means of cardiac gating (United States patent publication numbers 2007/0106149A1 and US2007/0106146A1). In cardiac gating, a single cardiac cycle is interpolated from a large number of images acquired over the course of numerous cardiac cycle events. Cardiac gating is applied to methods that do not image at significantly faster than cardiac rate, for example magnetic resonance imaging (MRI) and computed tomography (CT). The method of cardiac gating does not allow the reconstruction of a single vascular pulse wave in a single cardiac cycle, as does this disclosure, nor the interactions between vascular pulse waves that are adjacent in time, as does this disclosure.

A ramification of the need to acquire several minutes of data per the method of cardiac gating is that it does not allow the separate imaging of vascular pulse waves attached to the arterial versus venous component of circulation. The method of this disclosure can reconstruct individual vascular pulse waves. By reconstructing them according to the delay in timing of the travel of an angiographic bolus, this method can reconstruct separate arterial and venous pulse waves, since the angiographic components of circulation are distinct in their time of flight, where the arterial component of an injected contrast bolus arrives sooner than the venous component.

One aspect of this disclosure is to extract cardiac frequency angiographic phenomena from an angiogram obtained at higher than cardiac frequency. A further aspect of this disclosure to do so even in the setting where there is motion alias due to pulse motion of the vessels containing the angiographic contrast.

A brain angiogram is obtained at higher than cardiac rate. An intravascular bolus of a contrast agent is injected and the passage of the bolus is imaged at faster than cardiac rate. Each image is termed a frame, and each frame consists of n by m pixels. This gives an angiographic data set of q frames of images with n by m pixels. The q frames are obtained with uniform time sampling, which may be measured in Hertz.

In the current aspect, each datum in an angiographic study is indexed by two spatial and one time index. This corresponds to a time-indexed sequence of two-dimensional images. The methods of this disclosure are not limited to two spatial dimensions and could be extended to three spatial dimensions with obvious modifications.

The preferred aspect uses complex valued data elements and complex valued wavelet transforms. However, similar results could be obtained with real valued data elements and real valued wavelet transforms.

This paragraph comments on the use of complex numbers in the current aspect of this disclosure. After the method of this disclosure has been applied to an angiogram to give a spatiotemporal representation of cardiac frequency angiographic phenomena, each complex number in spatiotemporal grid element represents the result of a wavelet cardiac frequency filter applied to an angiogram. A complex number may be represented in polar coordinates with a magnitude, since for a complex number $c=a+ib$ that represents a cardiac frequency angiographic phenomenon at a given space-time grid element, it has a polar representation $\{|c|, \phi_d\}$ where the magnitude $|c|=\sqrt{a^2+b^2}$ may be rendered as brightness and $\phi_c$, the angle between the positive x-axis and the point $\{a, b\}$, representing the phase of the cardiac frequency phenomenon at that space time element, as hue. The color model for rendering a complex valued number in a pixel is depicted in FIG. 1. In particular, FIG. 1 shows a spectrum of color hues with a green region, a yellow region, a red region, and a blue region noted (although the image is submitted as grayscale, one of ordinary skill in the art would recognize that this grayscale image includes a spectrum of hues). A sequence of such images may be animated across the time indices to represent a cine video sequence of the motions of a train of vascular pulse waves in the brain.

The steps of this disclosure after the import into computer memory of an angiogram depend on the presence or absence of motion alias. If there is no significant tissue motion then there is no motion alias. Then a reconstruction without accommodation for motion alias is applied, which is described as follows.

The angiographic data consisting of n by m pixels by q frames data is imported into computer memory and reformatted with the processor in memory to give an n by m array of time signals each q samples long.

A complex valued wavelet transform is applied by the processor to each pixel-wise time signal, giving an n by m array of wavelet transforms.

The pixel-wise wavelet transforms are filtered for cardiac frequency by the processor. This is done by setting to zero all wavelet coefficients that do not correspond to cardiac wavelet scale (in the field of wavelets this term corresponds to the concept of cardiac frequency).

The pixel-wise wavelet transforms data are inverse wavelet transformed by the processor into time domain and reformatted in computer memory into q frames of n by m pixels. Each data element (voxel) in this three dimensional grid is a complex valued number.

Each frame can be rendered as an image with a brightness hue color model to represent the complex datum in each pixel by the processor.

Cardiac frequency magnitude is represented as brightness and phase as hue.

The q images may be rendered as motion cine by the processor or they may be stored as a video file format such as Quicktime by the processor. The data may be analyzed in other ways including as running phase histograms.

If there is motion alias, then a modified algorithm is applied by the processor to the angiographic data after it has been imported into computer memory as follows:

The sum angiographic signal for each time frame is summed by the processor for all n by m pixels to give an overall angiographic intensity point. This is performed for each of the q frames to give an overall angiographic time intensity curve of length q.

A high frequency resolution wavelet transform is applied by the processor to this single angiographic time intensity curve.

Then the angiographic data is reformatted by the processor in computer memory as an n by m array of time signals each of length q.

A high temporal wavelet transformation is performed by the processor on each such pixel-wise time signal. This step yields an n by m array of high temporal resolution wavelet transforms.

In wavelet domain, each pixel-wise high temporal resolution wavelet transform is cross correlated (by simple multiplication) by the single high frequency resolution wavelet transform of the overall angiographic time intensity curve by the processor.

This n by m array of cross-correlated signals in wavelet domain is inverse wavelet transformed to give an n by m array of time domain time signals each of length q by the processor. Each datum in this n by m by q grid is complex valued.

The n by m time signals of length a are reformatted by the processor in computer memory into q frames of n by m pixels, each complex valued.

Each frame may be rendered as an image with a brightness hue color model by the processor, as above, or otherwise subjected to further analysis.

These wavelet methods of spatiotemporal reconstruction of angiographic cardiac frequency phenomena, both for data with and without motion alias, were generated by computational testing with simulated angiographic data and have been verified against biological optical, ultrasound, and fluoroscopic angiographic data. The methods for generating and testing against simulated angiographic data are not the topic of this disclosure.

The disclosure accordingly comprises the several steps and the relation of one or more of such steps with respect to each of the others, and the apparatus embodying features of construction, combinations of elements and arrangement of parts that are adapted to affect such steps, all is exemplified in the following detailed disclosure, and the scope of the disclosure will be indicated in the claims.

A notation is introduced to simplify the description of this disclosure. The lower case symbols $C_{i,j,t}$ are used to denote pixel-wise time signals, in which case the pixel indices i,j may be implied. The upper case symbol $$C_t = \frac{1}{nm}\Sigma_{i,j}C_{i,j,t}$$

is used to denote the frame-wise angiographic time intensity signal where i and j each range from 1 to the pixel dimensions respectively n and m. For $C_t$ the subscript t may be implied for brevity. For $C_{i,j,t}$ any or all of the subscripts i, j, t are implied if not explicitly given for brevity. The symbol $C_{i,j}$ denotes the angiographic time intensity curve across time corresponding to the i, $j^{th}$ pixel.

This disclosure employs a notation employing over symbols to specify the resolution characteristic of a wavelet transform. A wavelet transform of unspecified temporal and frequency resolution is denoted by the over bar symbol , a high temporal resolution wavelet transform is denoted by the over hat symbol ˆ. A high frequency resolution wavelet transform is denoted with the over tilde symbol . Thus, for example, if the angiographic time intensity curve for the i, $j^{th}$ pixel is $C_{i,j}$, then its high temporal resolution wavelet transform is denoted by $\hat{C}_{i,j}$. For the overall angiographic time intensity curve C the high frequency resolution wavelet transform is denoted by $\tilde{C}$.

Figure 2:
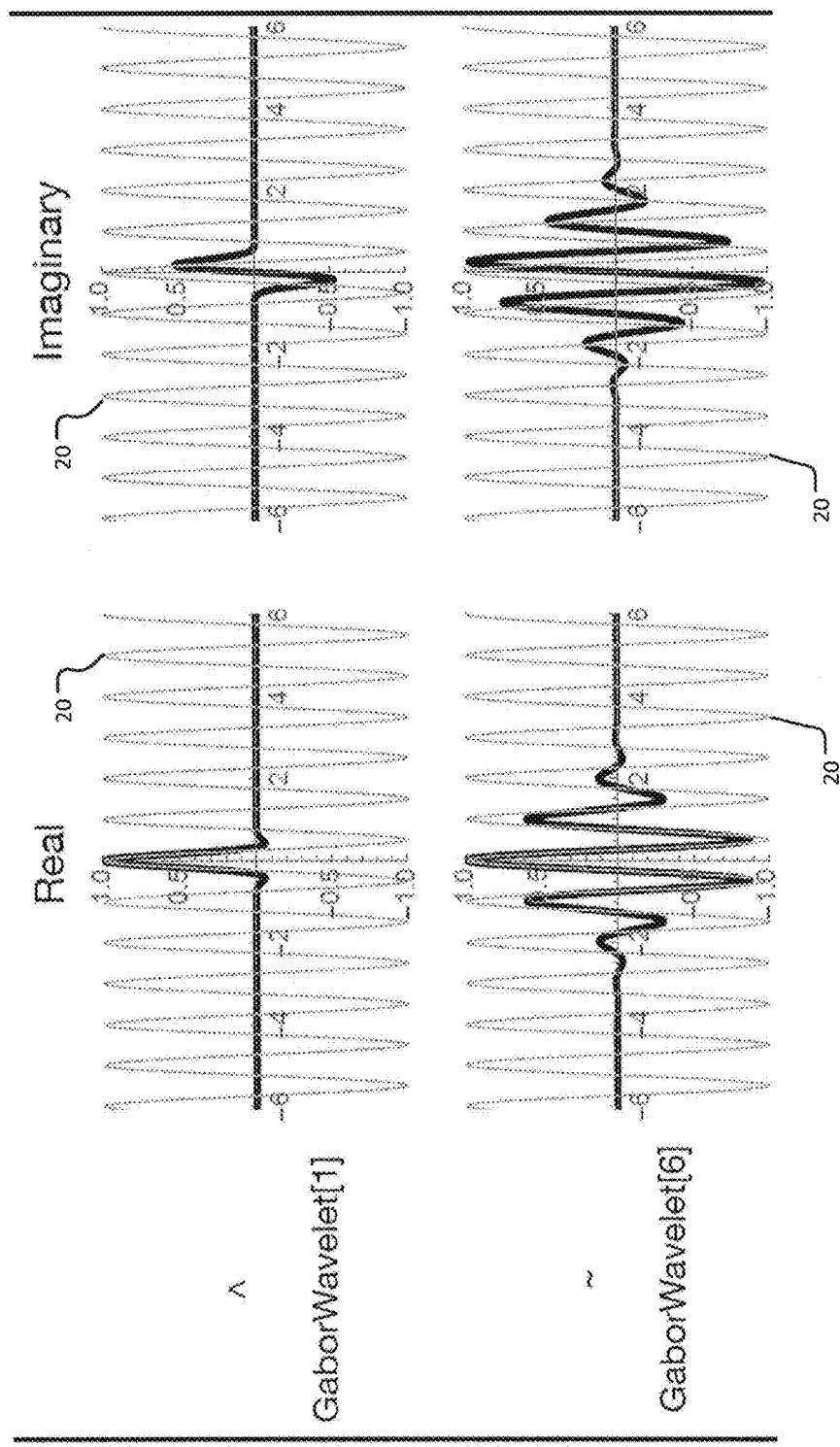
FIG. 2 illustrates a low and high temporal and frequency resolution wavelet ψs, where the orange curves 20 are cardiac frequency sinusoids according to aspects of the disclosure.

In the current aspect, the computational code is written in the Wolfram language and is executed in the Mathematica version 10 environment (Wolfram Research, Urbana, Ill., USA). This environment provides the wavelet library employed by the current aspect. The Wolfram function GaborWavelet [1] is employed to compute a high temporal resolution wavelet transform and the function GaborWavelet [6] is employed to compute a high frequency resolution wavelet transform. The real and imaginary components of the wavelet ψs employed by these functions are shown in FIG. 2.

Hereafter the detailed description of the current aspect is given with reference to the Wolfram language computer code that executes the steps of the disclosure. The Wolfram language favors the functional style of programming. The computer code is lightly edited for readability. Of course, other computational languages may be utilized as well.

In the current aspect, the raw angiographic data is supplied as a video file in the QuickTime format. It is imported into computer memory, changed from RGB color into grayscale by the processor, and each time-space grid element is changed into a floating point number ranging in [0., 1.] with the line:

angiographicFrames=Import["AngiographyVideoFileName.mov", "Data", "ColorSpace"->"Grayscale"] [[All, All, All, 1]]/256

The frame-wise angiographic data is reformatted by the processor and stored in computer memory as a pixel-wise array of angiographic time signals corresponding to $C_{i,j}$ with the line:

angiographicTimeSignals=Transpose[angiographicFrames, {3, 1, 2}]

Figure 3:
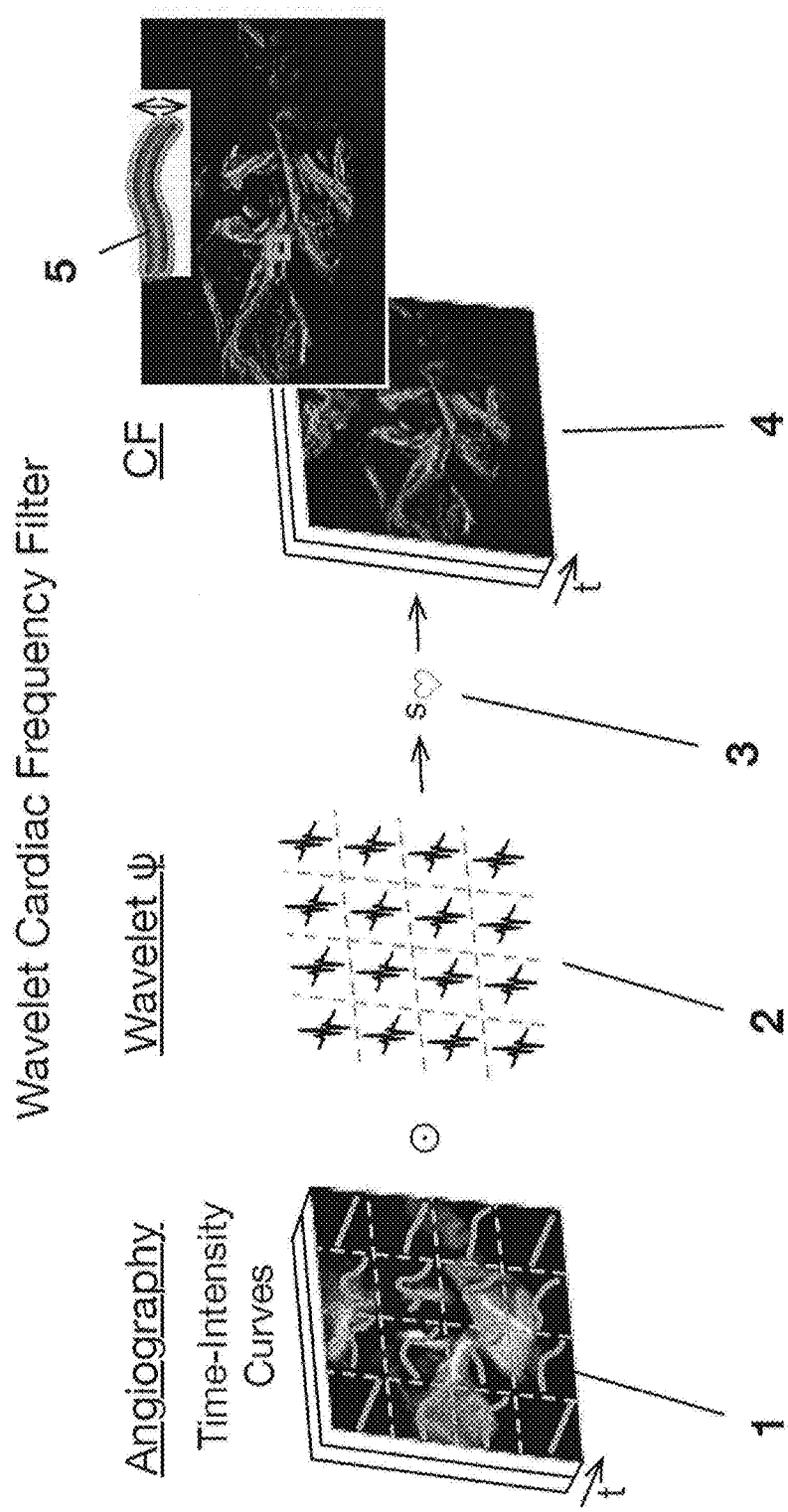
FIG. 3 illustrates wavelet spatiotemporal reconstruction of cardiac frequency angiographic phenomena according to aspects of the disclosure.

This step is illustrated by annotation [1] of FIG. 3.

The next step in the current aspect is the pixel-wise wavelet transforms and cardiac frequency filtering by extraction of the cardiac wavelet scale by the processor. These steps are illustrated respectively by annotations [2] and [3] of FIG. 3. The cardiac wavelet scale may be determined from the heart rate as obtained by any accepted physiological technique. The cardiac wavelet scale is closely related to the cardiac period (the reciprocal of the cardiac rate), and is represented in this computer code by the variable cardiacWaveletScale. The steps of pixel-wise wavelet transform, cardiac wavelet scale filtering, inverse wavelet transform, and data reformatting as video frames is performed by the processor by the line:

```
cardiacFrequencyAngiographicPhenomenaFrames = Transpose[
  Map[ InverseContinuousWaveletTransform[
    WaveletMapIndexed[ c -> 0 c,
    ContinuousWaveletTransform[ #, GaborWavelet[1]],
    Except[ cardiacWaveletScale]]] &, angiographicTimeSignals, {2}],
  {2, 3, 1}]
```

This computer code variable cardiacFrequencyAngiographicPhenomenaFrames contains the result after filtering for cardiac frequency angiographic phenomena. The pixel-wise inverse wavelet transforms and the frame-wise reformatting of the data are illustrated by annotation [4] of FIG. 3.

Since the original angiographic data are acquired at faster than cardiac frequency, the coherent spatiotemporal cardiac frequency phenomena present in it may represent single moving vascular pulse waves.

The detailed description of the method for the circumstance where there is significant motion alias follows. The presence of motion alias may be assessed from the presence of phase bimodality within the course of a single vessel. Motion alias is attenuated by the use of a high temporal resolution wavelet transform for the pixel-wise time signals. This injects frequency alias into the result. The frequency alias may be attenuated by the computation of "jointness" with a high frequency resolution wavelet transformation applied to a low noise physiological signal from the source. In the current aspect, the low noise signal is C. In the notation of this disclosure, the cardiac frequency angiographic phenomena with attenuated motion alias is calculated by the processor and stored in computer memory for the time signal at the i, $j^{th}$ pixel by the cross correlation of the pixel-wise high temporal resolution wavelet transforms $\hat{C}_{i,j}$ by the high frequency resolution overall angiographic intensity curve $\tilde{C}$ as $$\hat{c}_{i,j}\tilde{C}. \quad (1)$$

Figure 4:
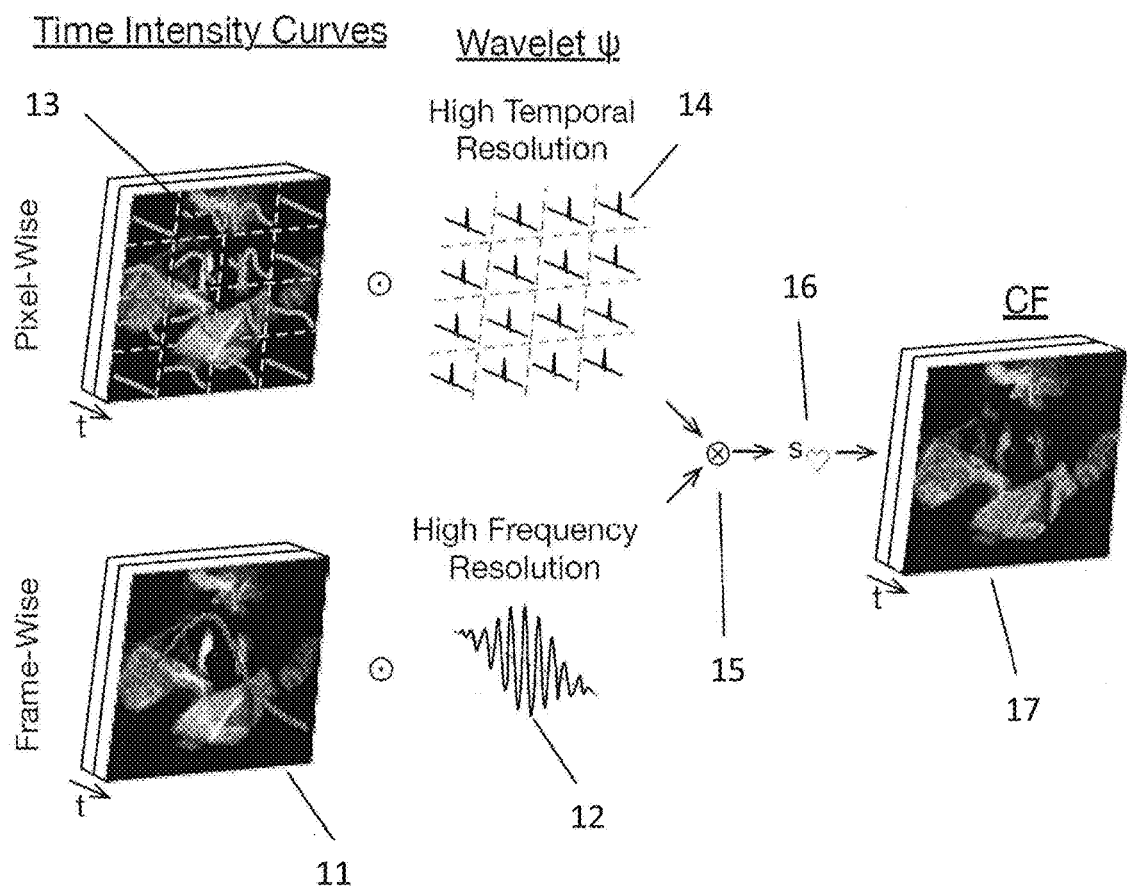
FIG. 4 illustrates wavelet spatiotemporal reconstruction of cardiac frequency angiographic phenomena where there is motion alias according to aspects of the disclosure.

Before proceeding with the pixel-wise high temporal resolution wavelet transforms, the overall angiographic time intensity curve denoted by is computed from the imported data with the line:
  angiographicTimeIntensityCurve=Mean/@angiographicFrames This step is illustrated by annotation [11] of FIG. 4. Its high frequency resolution wavelet transform denoted to be used later is computed as:
  tildeC=ContinuousWaveletTransform[angiographicTimeIntensityCurve, GaborWavelet[6]]

This step is illustrated by annotation [12] of FIG. 4.

In the current aspect, the wavelet cross-correlation is computed by the processor by the function written in the Wolfram language:

```
waveletCrossCorrelation[w1_ContinuousWaveletData,
  w2_ContinuousWaveletData] :=
  Block[ {xwd, normScale},
    If[ Not[w1['Wavelet']==w2['Wavelet']
```

```
      && w1['Octaves']==w2['Octaves']
      && w1['Voices']==w2['Voices']],
    Throw['wavelet arguments do not match']
    ];
    xwd = Conjugate[w1[_,'Values']] w2[_,'Values'];
    ContinuousWaveletData[
      Thread[w1['WaveletIndex']-> ((*normScale*) xwd)],
      w1['Wavelet'],
      'SampleRate'->w1['SampleRate']
      ]
  ]
```

With this function, the line that extracts cardiac frequency angiographic phenomena with attenuated motion alias based on $c_{i,j}\tilde{C}$ is:

```
cardiacFrequencyAngiographicPhenomenaFrames = Transpose[
  Map[
    InverseContinuousWaveletTransform[
    WaveletMapIndexed[c -> 0 c,
    waveletCrossCorrelation[tildeC,
      ContinuousWaveletTransform[#,
        GaborWavelet[1]]],
    Except[cardiacOctaveVoice]]] &,
  channelArray, {2}],
  {2, 3, 1}]
```

The steps of this Wolfram language computer code are illustrated in FIG. 4 by annotation [14], the pixel-wise high temporal resolution wavelet transforms, annotation [15], the cross-correlation of the pixel-wise high temporal resolution wavelet transforms by the single high frequency resolution wavelet transform of the overall angiographic intensity curve, annotation [16], the filtering by cardiac wavelet scale, and annotation [17], the pixel-wise inverse wavelet transforms, reformatting of the data as frame-wise, and the rendering of complex-valued data using a brightness-hue color model.

An angiographic bolus travels first through the arterial and then through the venous components of circulation. The angiographic time of flight, reflected in the notation of this disclosure by the time index, t, may thus be used to separate arterial from venous angiographic phenomena from the data grid represented in computer memory by the variable cardiacFrequencyAngiographicPhenomenaFrames.

Figure 5:
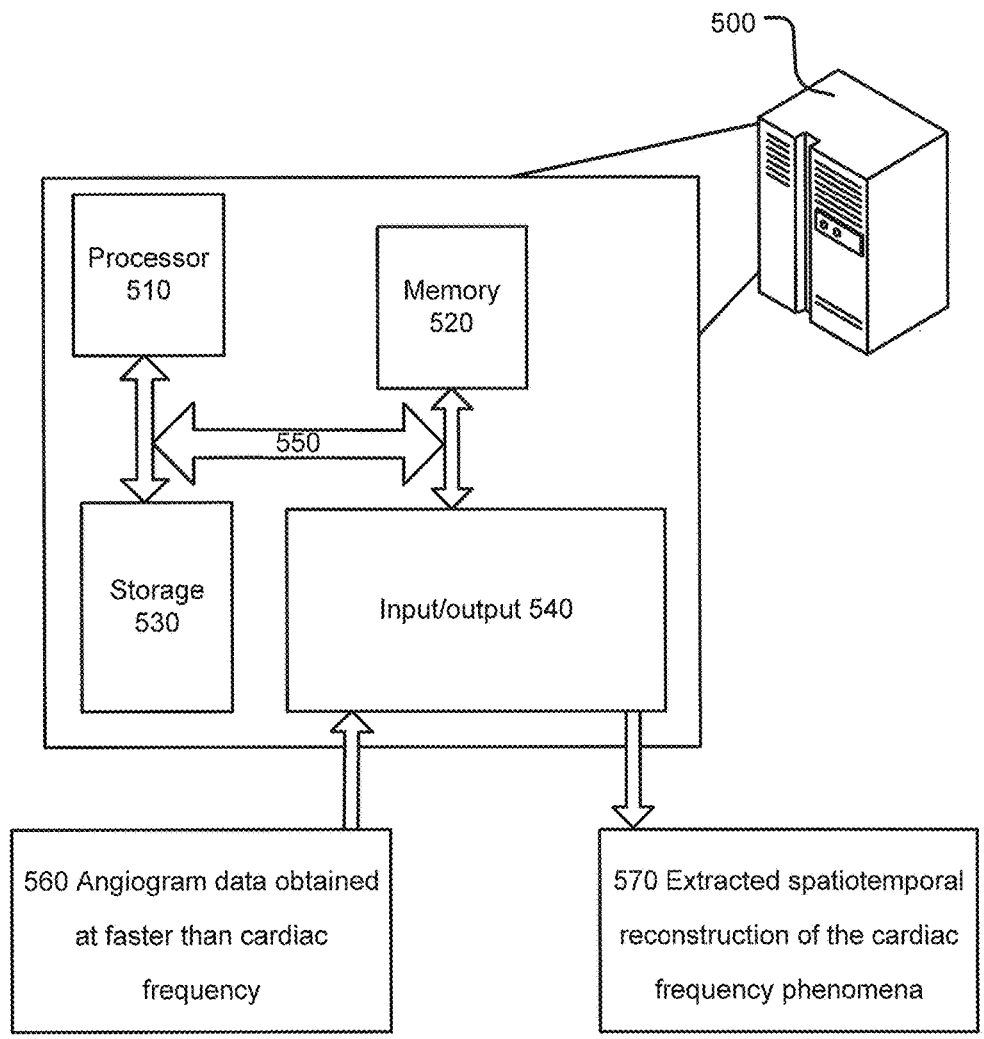
FIG. 5 shows a schematic diagram of an exemplary computer system for implementation of the disclosed process in accordance with aspects of the disclosure.

FIG. 5 shows a schematic diagram of an exemplary computer system in accordance with aspects of the disclosure. In particular, FIG. 5 illustrates a computer system 500 that can be used to implement the method to reconstruct the motions of vascular pulse waves in the brain. The computer system 500 includes a processor 510, a memory 520, a storage device 530, and an input/output device 540. Each of the components 510, 520, 530, and 540 can, for example, be interconnected using a system bus 550. The processor 510 is capable of processing instructions for execution of the method to reconstruct the motions of vascular pulse waves in the brain within the computer system 500. In one aspect, the processor 510 is a non-generic medical imaging processor. In one implementation, the processor 510 is a single-threaded processor. In another implementation, the processor 510 is a multi-threaded processor. The processor 510 is capable of processing instructions stored in the memory 520 or on the storage device 530 to reconstruct the motions of vascular pulse waves in the brain. In some aspects, a parallel processing set of computer systems 500 connected over a network may be employed, clustered into one or more server centers.

The input/output 540 may output the reconstructed motions of vascular pulse waves in the brain on a display, a printer, or the like. In one aspect, the input/output 540 may receive angiogram data obtained at faster than cardiac frequency 560. The angiogram data obtained at faster than cardiac frequency 560 may be processed by the processor 510 as noted above. The processor 510 producing extracted spatiotemporal reconstruction of the cardiac frequency phenomena 570. In one aspect, the input/output 540 may output the extracted spatiotemporal reconstruction of the cardiac frequency phenomena 570.

The memory 520 stores information within the computer system 500. In one implementation, the memory 520 is a computer-readable medium. In one implementation, the memory 520 is a volatile memory unit. In another implementation, the memory 520 is a non-volatile memory unit. The storage device 530 is capable of providing mass storage for the computer system 500. In one implementation, the storage device 530 is a computer-readable medium. In various different implementations, the storage device 530 can, for example, include a hard disk device, an optical disk device, or some other large capacity storage device. The input/output device 540 provides input/output operations for the computer system 500.

The resulting determined cardiac frequency angiographic phenomenon is used for comparison to target values to diagnose certain disorders. Moreover, the resulting determined cardiac frequency angiographic phenomenon is used for comparison to previous values to determine whether a particular medical treatment is beneficial, or the like. In this regard, it is believed that the ventricles of the brain, the largest anatomic structure without known primary function, serve to accommodate the passage of vascular pulse waves in the brain. Hydrocephalus, a disorder of the brain ventricles, affects about 1 in 500 live births but can occur at any age. The management of it is unsatisfactory and has not improved in decades. The disclosure will enhance the advancement of hydrocephalus management by determining why the brain has ventricles. Relatedly, intracranial pressure has a waveform but no one knows its basis. The disclosed method to image brain vascular pulse waves will help determine the basis of the intracranial pressure waveform. About 100,000 intracranial pressure monitoring systems are implanted in the USA per year for head trauma. These devices all capture a waveform of unknown significance.

The disclosure may be implemented in any type of computing devices, such as, e.g., a desktop computer, personal computer, a laptop/mobile computer, a personal data assistant (PDA), a mobile phone, a tablet computer, cloud computing device, and the like, with wired/wireless communications capabilities via the communication channels.

Further in accordance with various aspects of the disclosure, the methods described herein are intended for operation with dedicated hardware implementations including, but not limited to, PCs, PDAs, semiconductors, application specific integrated circuits (ASIC), programmable logic arrays, cloud computing devices, and other hardware devices constructed to implement the methods described herein.

It should also be noted that the software implementations of the disclosure as described herein are optionally stored on a tangible storage medium, such as: a magnetic medium such as a disk or tape; a magneto-optical or optical medium such as a disk; or a solid state medium such as a memory card or other package that houses one or more read-only (non-volatile) memories, random access memories, or other re-writable (volatile) memories. A digital file attachment to email or other self-contained information archive or set of archives is considered a distribution medium equivalent to a tangible storage medium. Accordingly, the disclosure is considered to include a tangible storage medium or distribution medium, as listed herein and including art-recognized equivalents and successor media, in which the software implementations herein are stored.

Additionally, the various aspects of the disclosure may be implemented in a non-generic computer implementation. Moreover, the various aspects of the disclosure set forth herein improve the functioning of the system as is apparent from the disclosure hereof. Furthermore, the various aspects of the disclosure involve computer hardware that it specifically programmed to solve the complex problem addressed by the disclosure. Accordingly, the various aspects of the disclosure improve the functioning of the system overall in its specific implementation to perform the process set forth by the disclosure and as defined by the claims.

The many features and advantages of the disclosure are apparent from the detailed specification, and, thus, it is intended by the appended claims to cover all such features and advantages of the disclosure which fall within the true spirit and scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A method of extracting cardiac frequency phenomena from an angiographic study obtained at faster than cardiac frequency, wherein in an instance of no significant motion alias by a wavelet transform of a pixel-wise time signals, filtering for cardiac wavelet scale, and inverse wavelet transformation.

2. A method of extracting cardiac frequency phenomena from an angiographic study obtained at faster than cardiac frequency, wherein in an instance of significant motion alias by a high temporal resolution wavelet transform of a pixel-wise time signals, a high frequency wavelet transform of the overall angiographic intensity curve, a pixel-wise wavelet cross correlation of these, filtering for cardiac wavelet scale, and inverse wavelet transformation.

3. A method of extracting cardiac frequency phenomena from an angiographic study obtained at faster than cardiac frequency, wherein in an instance of no significant motion alias, the method comprises:
    receiving angiographic data consisting of n by m pixels by q frames into computer memory;
    reformatting the angiographic data with a processor to generate an n by m array of time signals, each q samples long;
    applying a complex valued wavelet transform by the processor to each pixel-wise time signal to generate an n by m array of wavelet transforms;
    filtering the pixel-wise wavelet transforms for cardiac frequency by the processor;
    performing on the pixel-wise wavelet transforms data an inverse wavelet transform by the processor into time domain and reformatting into q frames of n by m pixels; and
    rendering each frame as an image with a brightness hue color model to represent a complex datum in each pixel with the processor.

4. A method of extracting cardiac frequency phenomena from an angiographic study obtained at faster than cardiac frequency, wherein in the instance of significant motion alias, the method comprises:
  summing an angiographic signal for each time frame by a processor for all n by m pixels to generate an overall angiographic intensity point for each of q frames to generate an overall angiographic time intensity curve of length q;
  applying a high frequency resolution wavelet transform by the processor to the angiographic time intensity curve;
  reformatting then angiographic data by the processor as an n by m array of time signals each of length q;
  performing a high temporal wavelet transformation by the processor on each pixel-wise time signal to generate an n by m array of high temporal resolution wavelet transforms;
  cross correlating in wavelet domain, each pixel-wise high temporal resolution wavelet transform by a single high frequency resolution wavelet transform of an overall angiographic time intensity curve by the processor;
  inverse wavelet transforming an n by m array of cross-correlated signals in wavelet domain to generate an n by m array of time domain time signals each of length q by the processor; and
  reformatting the n by m time signals of length a by the processor into q frames of n by m pixels, each complex valued.

5. A device for extracting cardiac frequency phenomena from an angiographic study obtained at faster than cardiac frequency wherein in an instance of no significant motion alias, the device comprises:
  a processor configured to receive angiographic data consisting of n by m pixels by q frames into a computer memory;
  the processor further configured to reformat the angiographic data to generate an n by m array of time signals, each q samples long;
  the processor further configured to apply a complex valued wavelet transform to each pixel-wise time signal to generate an n by m array of wavelet transforms;
  the processor further configured to filter the pixel-wise wavelet transforms for cardiac frequency;
  the processor further configured to perform on the pixel-wise wavelet transforms data an inverse wavelet transform into time domain and reformatting into q frames of n by m pixels; and
  the processor further configured to render each frame as an image with a brightness hue color model to represent a complex datum in each pixel.

6. A device for extracting cardiac frequency phenomena from an angiographic study obtained at faster than cardiac frequency, wherein in an instance of significant motion alias, the device comprises:
  a processor configured to sum the angiographic signal for each time frame by the processor for all n by m pixels to generate an overall angiographic intensity point for each of the q frames to generate an overall angiographic time intensity curve of length q;
  the processor further configured to apply a high frequency resolution wavelet transform to the angiographic time intensity curve;
  the processor further configured to reformat then the angiographic data as an n by m array of time signals each of length q;
  the processor further configured to perform a high temporal wavelet transformation on each such pixel-wise time signal to generate an n by m array of high temporal resolution wavelet transforms;
  the processor further configured to cross correlate in wavelet domain, each pixel-wise high temporal resolution wavelet transform by the single high frequency resolution wavelet transform of an overall angiographic time intensity curve;
  the processor further configured to inverse wavelet transform the n by m array of cross-correlated signals in wavelet domain to generate an n by m array of time domain time signals each of length q; and
  the processor further configured to reformat the n by m time signals of length a into q frames of n by m pixels, each complex valued.

* * * * *